United States Patent [19]

Berg et al.

[11] Patent Number: 5,780,648
[45] Date of Patent: Jul. 14, 1998

[54] BENZOTHIOPHENE COMPOUNDS, AND USES FORMULATIONS THEREOF

[75] Inventors: David Thompson Berg, Beech Grove; George Joseph Cullinan, Trafalgar; Brian William Grinnell, Indianapolis; Mark Alan Richardson, Bloomington, all of Ind.

[73] Assignee: Eli Lilly and Company, Indianapolis, Ind.

[21] Appl. No.: 882,674

[22] Filed: Jun. 25, 1997

Related U.S. Application Data

[60] Provisional application No. 60/021,785, Jul. 15, 1996.
[51] Int. Cl.$^6$ ............... C07D 333/56; C07D 333/64; A61K 31/38
[52] U.S. Cl. ................ 549/57; 549/54; 514/443
[58] Field of Search ............. 549/54, 57; 514/443

[56] References Cited

U.S. PATENT DOCUMENTS

| | | | |
|---|---|---|---|
| 3,594,478 | 7/1971 | Brandstrom et al. | 549/57 |
| 3,598,839 | 8/1971 | Kaltenbronn | 549/54 |
| 3,935,231 | 1/1976 | Avar et al. | 549/57 |
| 4,133,814 | 1/1979 | Jones et al. | 514/443 |
| 4,654,352 | 3/1987 | Ray | 514/443 |
| 5,175,184 | 12/1992 | Tomiyama et al. | 514/443 |
| 5,472,962 | 12/1995 | Koizumi et al. | 514/443 |
| 5,532,382 | 7/1996 | Carlson et al. | 549/57 |

*Primary Examiner*—Deborah C. Lambkin
*Attorney, Agent, or Firm*—James J. Sales; David E. Boone

[57] ABSTRACT

Benzothiophenes, and uses and formulations thereof, are provided by the present invention.

5 Claims, No Drawings

BENZOTHIOPHENE COMPOUNDS, AND USES FORMULATIONS THEREOF

This application claims the benefit of U.S. Provisional Application No. 60/021,785, filed Jul. 15, 1996.

BACKGROUND OF THE INVENTION

The fibrinolytic system plays a key role in maintaining normal hemostatic balance. A critical factor in this system is plasminogen activator inhibitor I (PAI-1), which reduces the endogenous ability to remove fibrin by inhibiting plasminogen activators such as tissue type plasminogen activator (tPA). Studies have documented that elevations of PAI-1 are associated with increased risk of deep venous thrombosis. Further, elevations in PAI-1 are found in patients suffering from myocardial infarction and septicemia. Because impaired fibrinolytic capacity is associated with increased cardiovascular risk, lowering PAI-1 should result in cardioprotection. In fact, recent studies on the analysis of PAI-1 levels in pre- and post-menopausal women in the Framingham Offspring Study have demonstrated that post-menopausal women have markedly higher PAI-1 levels, which can be reduced to pre-menopausal levels with estrogen therapy. This reduction in PAI-1 effect is believed to contribute to the overall effect of estrogen replacement therapy on the reduced risk of heart disease.

While PAI-1 can be produced in a variety of tissues, substantial levels are secreted by the vascular endothelial cell. The vascular endothelium constitutes a major organ that functions in the regulation of blood coagulation, inflammation and in the exchange of fluids and mediators between the intravascular compartment and parenchyma tissues. As such, the proper function of the endothelium is critical to overall homeostasis. Because PAI-1 can be increased in endothelial cells in response to certain stimuli, including cytokines, it contributes to a dysfunctional state that can result in coagulation defects, local and systemic vascular inflammation, and enhancement in the progression and rupture of atherosclerotic plaque. These effects can further result in conditions including myocardial infarction, deep venous thrombosis, and disseminated intravascular thrombosis.

Because the local control of PAI-1 at the endothelial cell/plasma interface can play a major role in many pathological processes, agents that inhibit the expression of PAI-1 in the endothelium could be useful in treating or preventing conditions such as sepsis, injuries involving major tissue damage and trauma, systemic inflammatory response syndrome, sepsis syndrome, septic shock and multiple organ dysfunction syndrome (including DIC) as well as myocardial infarction, deep venous thrombosis, disseminated intravascular thrombosis, atherosclerotic plaque rupture and its associated sequela.

In addition, tPA (tissue Plasiminogen Activator) is currently administered to patients who have suffered from conditions which place them at risk of detrimental thrombotic events. Exogenously administered tPA has been shown to be effective and is commercially available for treatment of such patients. However, efficacy with this therapy can be limited because PAI-1 inhibits the exogenously given tPA as well as the endogenously derived tPA. Therefore, it would be of great value if an agent were available which could either prolong the half-life or reduce the amount of exogenously administered tPA.

Further, because of the critical role of fibrin in tumor cell biology, agents that modulate PAI-1 may find use as anti-metastatic agents.

SUMMARY OF THE INVENTION

This invention provides compounds of formula I

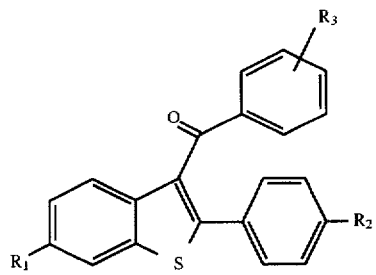

wherein $R_1$ and $R_2$ are independently —OH, —OCO ($C_1$–$C_6$ alkyl), —O(CO)O($C_1$–$C_6$ alkyl), —OCO-Ar, where Ar is phenyl or substituted phenyl, or —O(CO)Ophenyl; and $R_3$ is a substituent in the 3 or 4 position of the phenyl ring selected from the group of —H, —Cl, —Br, —$CH_3$, or —$CH_2CH_3$;

or a pharmaceutically acceptable salt or solvate thereof, with the proviso that when $R_1$ and $R_2$ are both hydroxy, $R_3$ is not —H, —$CH_3$, or —$CH_2CH_3$.

The invention also provides pharmaceutical formulations which include compounds of formula Ia.

The invention also provides methods of inhibiting PAI-1 or a physiological condition associated with an excess thereof, which includes administering to a human in need thereof an effective amount of a compound of formula Ib

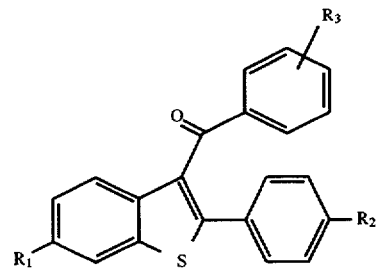

wherein $R_1$ and $R_2$ are independently —OH, —OCO ($C_1$–$C_6$ alkyl),—O(CO)O($C_1$–$C_6$ alkyl), —OCO-Ar, where Ar is phenyl or substituted phenyl, or —O(CO)Ophenyl; and $R_3$ is a substituent in the 3 or 4 position of the phenyl ring selected from the group of —H, —Cl, —Br, -$CH_3$, or —$CH_2CH_3$;

or a pharmaceutically acceptable salt or solvate thereof.

DETAILED DESCRIPTION OF THE INVENTION

The current invention concerns the discovery of (encompassing both Ia and Ib) 2-phenyl-3-aroyl-benzo[b] thiophenes, those of formula I, and their use for inhibiting PAI-1. The methods of use provided by this invention are practiced by administering to a human in need thereof a dose of a compound of formula I or a pharmaceutically acceptable salt or solvate thereof, that is effective to inhibit PAI-1 or a physiological condition associated with an excess thereof. The term "inhibit" includes its generally accepted meaning which includes prohibiting, preventing, restraining, and slowing, stopping, or reversing progression, severity, or ameliorating a resultant symptom or effect.

General terms used in the description of compounds herein described bear their usual meanings. For example, "$C_1$–$C_6$ alkyl" refers to straight or branched aliphatic chains of 1 to 6 carbon atoms including methyl, ethyl, propyl, iso-propyl, n-butyl, pentyl, iso-pentyl, hexyl, and the like.

The term "substituted phenyl" refers to a phenyl group having one or more substituents selected from the group consisting of $C_1$–$C_4$ alkyl, $C_1$–$C_3$ alkoxy, hydroxy, nitro, chloro, fluoro, or tri(chloro or fluoro)methyl. "$C_1$–$C_3$ alkoxy" refers a $C_1$–$C_3$ alkyl group attached through an oxygen bridge such as, methoxy, ethoxy, n-propoxy, isopropoxy.

Compounds of the invention include the following:

[2-(4-hydroxyphenyl)-6-hydroxybenzo[b]thien-3-yl][4-chlorophenyl]methanone

[2-(4-hydroxyphenyl)-6-hydroxybenzo[b]thien-3-yl][3-chlorophenyl]methanone

[2-(4-hydroxyphenyl)-6-hydroxybenzo[b]thien-3-yl][4-fluorophenyl]methanone

[2-(4-hydroxyphenyl)-6-hydroxybenzo[b]thien-3-yl][3-fluorophenyl]methanone

[2-(4-hydroxyphenyl)-6-hydroxybenzo[b]thien-3-yl][4-ethylphenyl]methanone

[2-(4-hydroxyphenyl)-6-hydroxybenzo[b]thien-3-yl][3-ethylphenyl]methanone

[2-(4-acetyloxyphenyl)-6-hydroxybenzo[b]thien-3-yl][4-methylphenyl]methanone

[2-(4-hydroxyphenyl)-6-acetyloxybenzo[b]thien-3-yl][4-methylphenyl]methanone

[2-(4-acetyloxyphenyl)-6-acetyloxybenzo[b]thien-3-yl][4-methylphenyl]methanone

[2-(4-hydroxyphenyl)-6-benzoyloxybenzo[b]thien-3-yl][4-chlorophenyl]methanone

A preferred embodiment of this invention is [2-(4-hydroxyphenyl)-6-hydroxybenzo[b]thien-3-yl][phenyl]methanone.

The compounds of formula I are derivatives of the benzo[b]thiophene structure which is named and numbered according to the Ring Index, The American Chemical Society, as follows:

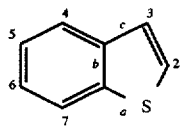

Compounds of the current invention may be synthesized in a manner similar to that illustrated in U.S. Pat. No. 4,133,814, incorporated herein by reference.

The following scheme is provided as an example of one route of synthesis of the compounds of formula I.

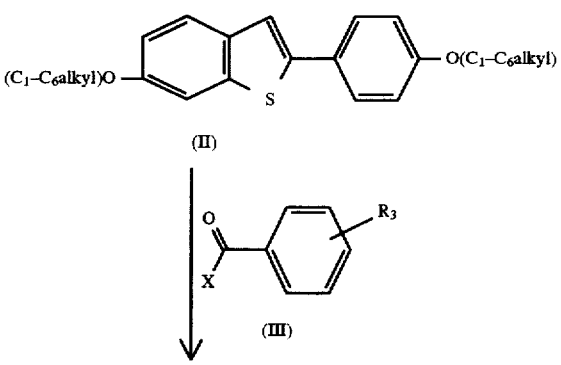

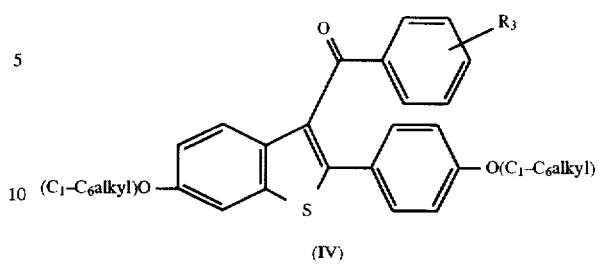

The compound of formula II may be prepared as set out in columns 16–17 of U.S. Pat. No. 4,133,814. Also, preparation 1 herein illustrates one method of forming a compound of formula II.

The 3-benzoyl moiety is introduced by acylation with an activated benzoic acid derivative (formula III) under standard Friedel-Crafts conditions, i.e., in the presence of a Lewis acid in an appropriate solvent. X may be chloro, bromo, a mixed anhydride, or the like. A preferred activated benzoic acid is an acid chloride and a preferred Lewis acid is $AlCl_3$. This procedure yields the compounds of formula IV and is illustrated in Preparation 2.

The alkoxyl groups at the 6 and 4' positions may be removed to yield compounds of formula I where $R_1$ and $R_2$ are both hydroxy, with agents such as $AlCl_3$, $BCl_3$, pyridine hydrochloride or the like, by methods well known in the art. Such a deprotection is illustrated in Examples 1, 2, and 3.

The other compounds of formula I may be derived from the 6, 4'-dihyroxycompounds by acylating with the appropriate agents, such as acetyl chloride, benzoyl chloride, and the like, and isolating the various isomers by convention chromatographic techniques, such as silica gel column chromatography. For example, mono-acetyl derivatives may be prepared by the reaction of one equivalent of acetyl chloride with a compound of formula Ia and the various isomers may separated by chromatography on silica gel eluted with EtOAc-hexane. Other methods are known in the art related to protecting and deprotecting hydroxyl functions (see: e.g., J. W. Barton, "Protective Groups in Organic Chemistry;, J. G. W. McOmie (ed.), Plenum Press, New York, N.Y., 1973, Chapter 2, and T. W. Green, "Protective Groups in Organic Synthesis", John Wiley and Sons, New York, N.Y., 1981, Chapter 7).

PREPARATION 1

2-(4-Methoxyphenyl)-6-methoxybenzo[b]thiophene

To 700 mL of EtOH were added 50 g (0.356 mmol) of 3-methoxythiophenol. To the mixture then were added 20 g (o.36 mmol) of KOH pellets followed by 82.5 g (0.36 mmol) of a-bromo-4-methoxyacetophenone added in small portions. The entire addition was carried out at about 25° C. Upon completion of the addition, the reaction mixture was stirred for three hours at room temperature. The EtOH was evaporated, and a residual oil was taken up in 2 L of water and 1.5 L of ether. The ether was separated, washed with water, dried over $MgSO_4$, and evaporated to dryness. The resulting crystalline residue was homogenized in a blender using a 3:1 mixture of ether and petroleum ether. The solid was filtered and dried to give 78.5 g (76%) of a-(3-methoxyphenylthio)-4-methoxyacetophenone as pink crystals.

MP: 53°–54° C.

EA: Calc. for $C_{16}H_{16}O_3S$: C, 66.64; H, 5.59; O, 16.64; S, 11.12 Found: C, 66.55; H, 5.87; O, 16.82; S, 10.86.

The above product was cyclized and isomerized by adding 50 g (0.173 mmol) of the product to 250 g of polyphosphoric acid preheated to 950 C. The mixture was vigorously stirred, and the temperature rose to 115°–120° C. Monitoring by tlc indicated that the reaction was virtually over after five minutes. At the end of thirty minutes, ice was added to the mixture. The temperature then rose to 130° C. at which time additional ice was added. Crystals appeared: water was added to the mixture, and the product was collected by filtration. The resulting tan solid was slurried in hot MeOH, cooled, and filtered. The solid was recrystallized from 2.5 L of EtOAc to obtain 30 g of the title compound.
MP: 193°–194° C.
EA: Calc. for $C_{16}H_{14}O_2S$: C, 71.08; H, 5.22; O, 11.84; S, 11.86 Found: C, 71.03; H, 5.30; O, 11.81; S, 11.60.

PREPARATION 2

|2-(4-Methoxyphenyl)-6-methoxybenzo|b|thien-3-yl||phenyl|methanone 3 g (11.1 mmol) of 2-(4-methoxyphenyl)-6-methoxybenzo|b|thiophene and 1.55 g (11.1 mmol) of benzoyl chloride were suspended in 150 mL of $CH_2Cl_2$ and cooled to 0° C. The reaction mixture was vigorously stirred and 1.6 g (12 mmol) of $AlCl_3$ was added in several portions over a ten minute time period. The reaction was allowed to proceed for one hour, after which 1 L of water was added to quench the reaction. The organic layer was separated and washed with 100 mL of 1N NaOH, 100 mL of brine, dried by filtration through anhydrous $K_2CO_3$, and evaporated to dryness. The crude product was crystallized twice from MeOH. This yielded 1.85 g of the title compound as white crystalline solid.
MP: 100°–102° C.
PMR: Consistent with the proposed structure.

EXAMPLE 1

|2-(4-Hydroxyphenyl)-6-hydroxybenzo|b|thien-3-yl| |phenyl|methanone 2.5 g (6.7 mmol) of |2-(4-methoxyphenyl)-6-methoxybenzo|b|thien-3-yl||phenyl| methanone mixed with 10 g of pyridine hydrochloride and fused at 220° C. for 1.5 hours. The reaction mixture was poured into ice-water and mixture extracted with 500 mL of EtOAc. The EtOAc layer was separated, washed with brine, dried with $MgSO_4$, and evaporated to a yellow oil. The product was crystallized from MeOH—HOH. This yielded 2.1 g of the title compound as yellow crystalline solid.
MP: 203°–205° C.
PMR: Consistent with the proposed structure.
MS: m/e=346 (M)
EA: Calc. for $C_{21}H_{14}O_3S$: C, 72.81; H, 4.07; O, 13.86; S, 9.26 Found: C, 72.54; H, 4.09; O, 13.80; S, 9.23.

PREPARATION 3

|2-(4-Methoxyphenyl)-6-methoxybenzo|b|thien-3-yl||3-methylphenyl|methanone

In a manner similar to that described in Preparation 2, 3.1 g (20 mmol) of 3-methylbenzoylchloride, 2 g (7.4 mmol) of 2-(4-methoxyphenyl)-6-methoxybenzo|b|thiophene and 6.7 g (50 mmol) of $AlCl_3$ were converted to 4.7 g of the title compound, isolated as yellow amorphous powder.
PMR: Consistent with the proposed structure.
MS: m/e=388 (M) FD EA: Calc. for $C_{24}H_{20}O_3S$: C, 74.20; H, 5.19 Found: C, 74.46; H, 5.33.

EXAMPLE 2

|2-(4-Hydroxyphenyl)-6-hydroxybenzo|b|thien-3-yl| |3-methylphenyl|methanone 1 g (3 mmol) of |2-(4-methoxyphenyl)-6-methoxybenzo|b|thien-3-yl||3-methylphenyl|methanone was dissolved in 29 mL of $CH_2Cl_2$ and cooled to −70° C. To the stirring solution was added 20 mL of 1M BBr3 in $CH_2Cl_2$ in small portions over a ten minute period. The reaction was allowed to proceed under a nitrogen atmosphere, slowly warming to ambient temperature. After sixteen hours, the reaction was quenched by adding 1N NaOH and extracted with 200 mL of EtOAc. The EtOAc layer was separated and washed with water, dried by filtration through anhydrous $Na_2SO_4$, and evaporation to dryness, in vaccuo. The crude product was purified by chromatography on a silica gel column eluted with EtOAc-hexane (1:4)(v/v). The product was rechromatographed on a silica gel column eluted with EtOAc-hexane (1:3)(v/v). This yielded 190 mg of the title compound as a yellow amorphous powder.
PMR: Consistent with the proposed structure.
MS: m/e=360 (M) FD.

PREPARATION 4

|2-(4-Methoxyphenyl)-6-methoxybezo|b|thien-3-yl| |4-methylphenyl|methanone

In a manner similar to that used in Preparation 3, 2.32 g (15 mmol) of 4-methylbenzoyl chloride, 2 g (7.4 mmol) of 2-(4-methoxyphenyl)-6-methoxybenzo|b|thiophene, and 5.3 g (40 mmol) of $AlCl_3$ were converted to 1.9 g of the title compound, crystallized from $Et_2O$ and isolated as a light yellow powder.
PMR: Consistent with the proposed structure.
MS: m/e=388 (M) FD
EA: Calc. for $C_{24}H_{20}O_3S$: C, 74.20; H, 5.19 Found: C, 73.85; H, 5.20.

EXAMPLE 3

|2-(4-Hydroxyphenyl)-6-hydroxybenzo|b|thien-3-yl| |4-methylphenyl|methanone

In a manner similar to that used in Example 2, 1 g (3 mmol) of |2-(4-methoxyphenyl)-6-methoxybezo|b|thien-3-yl||4-methylphenyl|methanone was converted with 20 mL of 1M $BBr_3$ in $CH_2Cl_2$ to 700 mg of the title compound. The final product was isolated a light yellow amorphous powder.
PMR: Consistent with the proposed structure.
MS: m/e=360 (M) FD.

Compounds of the current invention are well suited to form base addition salts. Bases commonly used for formation of salts include ammonium hydroxide and alkali and alkaline earth metal hydroxides, carbonates, as well as aliphatic and primary, secondary and tertiary amines, aliphatic diamines. Bases especially useful in the preparation of addition salts include ammonium hydroxide, potassium carbonate, methylamine, diethylamine, ethylene diamine and cyclohexylamine.

The pharmaceutically acceptable base addition salts are typically formed by reacting a compound of formula I with an equimolar or excess amount of base. The reactants are generally combined in a mutual solvent such as diethyl ether, EtOAc, alcohols or benzene. The salt normally precipitates out of solution within about one hour to 10 days and can be isolated by filtration or the solvent can be stripped off by conventional means.

The pharmaceutically acceptable salts generally have enhanced solubility characteristics compared to the compound from which they are derived, and thus are often more amenable to formulation as liquids or emulsions.

Pharmaceutical formulations can be prepared by procedures known in the art. For example, the compounds can be formulated with common excipients, diluents, or carriers, and formed into tablets, capsules, suspensions, powders, and the like. Examples of excipients, diluents, and carriers that are suitable for such formulations include the following: fillers and extenders such as starch, sugars, mannitol, and silicic derivatives; binding agents such as carboxymethyl cellulose and other cellulose derivatives, alginates, gelatin, and polyvinyl pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

The compounds can also be formulated as elixirs or solutions for convenient oral administration or as solutions appropriate for parenteral administration, for instance by intramuscular, subcutaneous or intravenous routes. Additionally, the compounds are well suited to formulation as sustained release dosage forms and the like. The formulations can be so constituted that they release the active ingredient only or preferably in a particular part of the intestinal tract, possibly over a period of time. The coatings, envelopes, and protective matrices may be made, for example, from polymeric substances or waxes.

The particular dosage of a compound of formula I required to inhibit PAI-1, or any other use disclosed herein, and according to this invention will depend upon the severity of the condition, the route of administration, and related factors that will be decided by the attending physician. Generally, accepted and effective daily doses will be from about 0.1 to about 1000 mg/day, and more typically from about 50 to about 200 mg/day. Such dosages will be administered to a subject in need thereof from once to about three times each day, or more often as needed to effectively inhibit PAI-1, or any other use disclosed herein.

Formulations

In the formulations which follow, "Active ingredient" means a compound of formula I.

Formulation 1: Gelatin Capsules
Hard gelatin capsules are prepared using the following:

| Ingredient | Quantity (mg/capsule) |
| --- | --- |
| Active ingredient | 0.1–1000 |
| Starch, NF | 0–650 |
| Starch flowable powder | 0–650 |
| Silicone fluid 350 centistokes | 0–15 |

The ingredients are blended, passed through a No. 45 mesh U.S. sieve, and filled into hard gelatin capsules.

The specific formulations above may be changed in compliance with the reasonable variations provided.

A tablet formulation is prepared using the ingredients below:

Formulation 2: Tablets

| Ingredient | Quantity (mg/tablet) |
| --- | --- |
| Active ingredient | 0.1–1000 |
| Cellulose, microcrystalline | 0–650 |
| Silicon dioxide, fumed | 0–650 |
| Stearate acid | 0–15 |

The components are blended and compressed to form tablets.

Alternatively, tablets each containing 0.1–1000 mg of active ingredient are made up as follows:

Formulation 3: Tablets

| Ingredient | Quantity (mg/tablet) |
| --- | --- |
| Active ingredient | 0.1–1000 |
| Starch | 45 |
| Cellulose, microcrystalline | 35 |
| Polyvinylpyrrolidone (as 10% solution in water) | 4 |
| Sodium carboxymethyl cellulose | 4.5 |
| Magnesium stearate | 0.5 |
| Talc | 1 |

The active ingredient, starch, and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° C. and passed through a No. 18 mesh U.S. sieve. The sodium carboxymethyl starch, magnesium stearate, and talc, previously passed through a No. 60 U.S. sieve, are then added to the granules which, after mixing, are compressed on a tablet machine to yield tablets.

Suspensions each containing 0.1–1000 mg of medicament per 5 mL dose are made as follows:

Formulation 4: Suspensions

| Ingredient | Quantity (mg/5 ml) |
| --- | --- |
| Active ingredient | 0.1–1000 mg |
| Sodium carboxymethyl cellulose | 50 mg |
| Syrup | 1.25 mg |
| Benzoic acid solution | 0.10 mL |
| Flavor | q.v. |
| Color | q.v. |
| Purified water to | 5 mL |

The medicament is passed through a No. 45 mesh U.S. sieve and mixed with the sodium carboxymethyl cellulose and syrup to form a smooth paste. The benzoic acid solution, flavor, and color are diluted with some of the water and added, with stirring. Sufficient water is then added to produce the required volume.

To demonstrate the utility for the compounds of formula I in inhibiting PAI-1, the following experimental procedure was performed.

Endothelial Cell PAI-1 Assay 96 well tissue culture plates were prepared with $1 \times 10^4$ human endothelial cells (HUVEC) per well in Clonetics' Endothelial Cell Growth Medium (EGM) supplemented with 2% FBS. Following incubation overnight at 37_C., the medium was replaced with serum-free medium (DMEM/F-12 medium, 20 mM-HEPES, pH 7.5, 50 µg/ml gentamicin, 1 μg/ml human transferrin and 1 μg/ml bovine insulin) with or without compound 1, (where $R_1$ and $R_2$ are hydroxy, and $R_3$ is hydrogen), and with or without 1 nM IL-1-beta. Following incubation overnight at 37_C., samples of culture medium were assayed for secreted PAI-1 using the Imubind Plasma PAI-1 ELISA (American Diagnostic Inc. #822/1S).

Results

Human umbilical vein endothelial cells (HUVEC) were treated with compound 1 (Example 1) concurrent to the induction of PAI-1 with IL-1. In initial experiments with several lots of cells obtained from a commercial supplier (Clonetics), we found that not all lots were responsive to 17-beta estradiol, and were thus not used in experiments to determine the effect of compound 1 on PAI-1 secretion. As shown in Table 1, using an estrogen-responsive line, we observed that compound 1 significantly reduced the induction of PAI-1 by IL-1 at a concentration of 1 nM. These data demonstrate that compound 1 is a potent inhibitor of the induction of PAI-1 from activated endothelial cells and should result in a cardioprotective effect, i.e. reduction in the incidence of cardiovascular events, due to enhancing fibrinolytic potential. Further the positive effect of compound 1 on reducing PAI-1 may provide for acute and chronic uses in conditions where elevated levels are associated with pathology or may be used to prevent such pathological conditions.

TABLE 1

Effect of compound 1 on PAI-1 secretion from human endothelial cells

| Treatment | PAI-1 Induction % of IL-1 Control +/- SE* |
| --- | --- |
| IL-1 Control | 100 |
| IL-1 & 1 nM Compound 1 | 44 +/- 8 |
| IL-1 & 10 nM compound 1 | 36 +/- 5 |

*(drug treated − control)/(Il-1 treated − control) × 100%

We claim:
1. A compound of formula Ia:

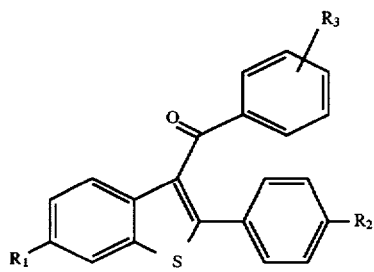

wherein $R_1$ and $R_2$ are independently —OH, —OCO ($C_1$-$C_6$ alkyl), —O(CO)O($C_1$-$C_6$ alkyl), —OCO—Ar, where Ar is phenyl or substituted phenyl, or —O(CO) Ophenyl; and $R_3$ is a substituent in the 3 or 4 position of the phenyl ring selected from the group of —H, —Cl, —Br, —$CH_3$, or —$CH_2CH_3$;

or a pharmaceutically acceptable salt or solvate thereof, with the proviso that when $R_1$ and $R_2$ are both hydroxy, $R_3$ is not —H, —$CH_3$, or —$CH_2CH_3$.

2. A compound of formula Ia of claim 1 selected from

|2-(4-hydroxyphenyl)-6-hydroxybenzo|b|thien-3-yl||4-chlorophenyl|methanone

|2-(4-hydroxyphenyl)-6-hydroxybenzo|b|thien-3-yl||3-chlorophenyl|methanone

|2-(4-hydroxyphenyl)-6-hydroxybenzo|b|thien-3-yl||4-fluorophenyl|methanone

|2-(4-hydroxyphenyl)-6-hydroxybenzo|b|thien-3-yl||3-fluorophenyl|methanone

|2-(4-acetyloxyphenyl)-6-hydroxybenzo|b|thien-3-yl||4-methylphenyl|methanone

|2-(4-hydroxyphenyl)-6-acetyloxybenzo|b|thien-3-yl||4-methylphenyl|methanone

|2-(4-acetyloxyphenyl)-6-acetyloxybenzo|b|thien-3-yl||4-methylphenyl|methanone or

|2-(4-hydroxyphenyl)-6-benzoyloxybenzo|b|thien-3-yl||4-chlorophenyl|methanone.

3. A pharmaceutical formulation comprising a compound of formula Ia of claim 1 and one or more excipients, diluents or carriers.

4. A method of inhibiting PAI-1 or a physiological condition associated with an excess thereof comprising administering to a human in need thereof an effective amount of a compound of formula Ib

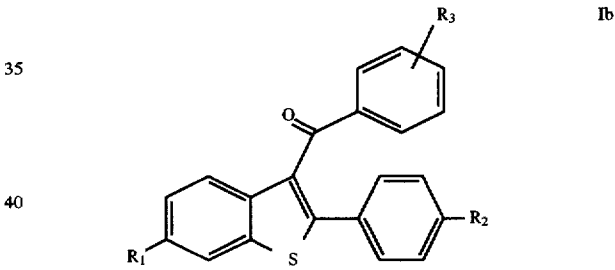

wherein $R_1$ and $R_2$ are independently —OH, —OCO ($C_1$-$C_6$ alkyl), —O(CO)O($C_1$-$C_6$ alkyl), —OCO—Ar, where Ar is phenyl or substituted phenyl, or —O(CO) Ophenyl; and $R_3$ is a substituent in the 3 or 4 position of the phenyl ring selected from the group of —H, —Cl, —Br, —$CH_3$, or —$CH_2CH_3$;

or a pharmaceutically acceptable salt or solvate thereof.

5. The method according to claim 4 wherein said compound is |2-(4-hydroxyphenyl)-6-hydroxybenzo|b|thien-3-yl||phenyl|methanone.

* * * * *